US 7,905,827 B2

(12) United States Patent
Uchiyama et al.

(10) Patent No.: US 7,905,827 B2
(45) Date of Patent: *Mar. 15, 2011

(54) ENCAPSULATED ENDOSCOPE SYSTEM IN WHICH ENDOSCOPE MOVES IN LUMEN BY ITSELF AND ROTATION OF IMAGE OF REGION TO BE OBSERVED IS CEASED

(75) Inventors: Akio Uchiyama, Saitama (JP); Hironobu Takizawa, Hachioji (JP); Takeshi Yokoi, Hino (JP); Hitoshi Mizuno, Koganei (JP)

(73) Assignee: Olympus Corporation, Tokyo (JP)

( * ) Notice: Subject to any disclaimer, the term of this patent is extended or adjusted under 35 U.S.C. 154(b) by 1262 days.

This patent is subject to a terminal disclaimer.

(21) Appl. No.: 11/496,560

(22) Filed: Jul. 31, 2006

(65) Prior Publication Data

US 2006/0270903 A1 Nov. 30, 2006

Related U.S. Application Data

(63) Continuation of application No. 10/409,329, filed on Apr. 8, 2003, now Pat. No. 7,122,001.

(30) Foreign Application Priority Data

Apr. 8, 2002 (JP) ................... 2002-105493

(51) Int. Cl.
*A61B 1/00* (2006.01)
*A61B 1/04* (2006.01)
*A61B 1/06* (2006.01)
(52) U.S. Cl. .................... 600/103; 600/117; 600/160
(58) Field of Classification Search .................. 600/109, 600/117, 118, 160
See application file for complete search history.

(56) References Cited

U.S. PATENT DOCUMENTS

| | | | |
|---|---|---|---|
| 5,188,111 A | 2/1993 | Yates et al. | |
| 5,347,987 A | 9/1994 | Feldstein et al. | |
| 5,429,132 A | 7/1995 | Guy et al. | |
| 5,469,840 A | 11/1995 | Tanii et al. | |
| 5,681,260 A | 10/1997 | Ueda et al. | |
| 5,899,851 A | 5/1999 | Koninckx | |
| 5,989,230 A | 11/1999 | Frassica | |
| 6,240,312 B1 | 5/2001 | Alfano et al. | |
| 6,471,637 B1 | 10/2002 | Green et al. | |
| 6,511,417 B1 | 1/2003 | Taniguchi et al. | |
| 2002/0093484 A1* | 7/2002 | Skala et al. ............. | 345/163 |
| 2002/0111546 A1* | 8/2002 | Cook et al. .............. | 600/322 |
| 2002/0161280 A1 | 10/2002 | Chatenever et al. | |
| 2002/0165592 A1 | 11/2002 | Glukhovsky et al. | |

FOREIGN PATENT DOCUMENTS

| | | |
|---|---|---|
| JP | 2-70099 | 3/1990 |
| JP | 04-008342 | 1/1992 |
| JP | 3017770 | 12/1999 |
| JP | 2001-017388 | 1/2001 |
| JP | 2001-179700 | 7/2001 |

* cited by examiner

*Primary Examiner* — Thomas J Sweet
*Assistant Examiner* — Philip R Smith
(74) *Attorney, Agent, or Firm* — Scully, Scott, Murphy & Presser, P.C.

(57) ABSTRACT

An encapsulated endoscope system in accordance with the present invention comprises: an encapsulated endoscope that rotates to develop a thrust; a controller that moves the encapsulated endoscope in an intended direction of advancement; an imaging unit incorporated in the encapsulated endoscope; and an image processing unit that receives image data sent from the imaging unit, and produces an image, which results from rotation of the received image data, according to the rotational phase of the encapsulated endoscope.

9 Claims, 20 Drawing Sheets

FIG.7

| FIRST IMAGE DATA | SECOND IMAGE DATA | THIRD IMAGE DATA | - - - | n-1-TH IMAGE DATA | n-TH IMAGE DATA |

FIG.8

| FIRST MAGNETIC FIELD DATA | SECOND MAGNETIC FIELD DATA | THIRD MAGNETIC FIELD DATA | - - - | n-1-TH MAGNETIC FIELD DATA | n-TH MAGNETIC FIELD DATA |

FIRST IMAGE    FIRST IMAGE'    FIRST IMAGE"

DISPLAY IMAGE

COIL TO BE DRIVEN

COIL TO BE DRIVEN

ENCAPSULATED ENDOSCOPE SYSTEM IN WHICH ENDOSCOPE MOVES IN LUMEN BY ITSELF AND ROTATION OF IMAGE OF REGION TO BE OBSERVED IS CEASED

This application is a continuation application of U.S. Ser. No. 10/409,329, filed on Apr. 8, 2003, now U.S. Pat. No. 7,122,001 which claims the benefit of Japanese Application No. 2002-105493 filed in Japan on Apr. 8, 2002, the contents of each of which are incorporated herein by reference.

BACKGROUND OF THE INVENTION

1. Field of the Invention

The present invention relates to an encapsulated endoscope system for driving and controlling an encapsulated endoscope that moves in a lumen by itself to image a region to be observed.

2. Description of the Related Art

For example, Japanese Unexamined Patent Application Publication No. 2001-179700 discloses a movement control system for movable micro-machines. The movement control system comprises: a magnetic field generating section that generates a rotating magnetic field; a robot that rotates on receipt of the rotating magnetic field generated by the magnetic field generating section so as to develop a thrust; a position detecting section that detects the position of the robot; and a magnetic field deflecting section that changes the orientation of the rotating magnetic field generated by the magnetic field generating section so as to move the robot in the direction of a destination.

SUMMARY OF THE INVENTION

According to the present invention, an encapsulated endoscope system comprises: an encapsulated endoscope that rotates to develop a thrust; a controller that moves the encapsulated endoscope in an intended direction of advancement; an imaging unit incorporated in the encapsulated endoscope; and an image processing unit that receives image data sent from the imaging section, and produces an image, which results from turning of the received image data, according to a rotational phase of the encapsulated endoscope.

Other features of the present invention and advantages thereof will be fully apparent from the description below.

BRIEF DESCRIPTION OF THE DRAWINGS

FIG. 1 to FIG. 16 are concerned with a first embodiment of the present invention;

FIG. 1 shows the outward configuration of an encapsulated endoscope system;

FIG. 2 is a block diagram showing the configuration of the capsulated endoscope system shown in FIG. 1;

FIG. 3 shows the outward form of an encapsulated endoscope included in the system shown in FIG. 2;

FIG. 4 is an explanatory diagram showing the encapsulated endoscope shown in FIG. 3;

FIG. 5 is a first flowchart describing processing to be performed in the encapsulated endoscope system shown in FIG. 2;

FIG. 6 is a second flowchart describing processing to be performed in the encapsulated endoscope system shown in FIG. 2;

FIG. 7 is a first explanatory diagram illustrating the effect of the processing described in FIG. 5 and FIG. 6;

FIG. 8 is a second explanatory diagram illustrating the effect of the processing described in FIG. 5 and FIG. 6;

FIG. 9 is a third explanatory diagram illustrating the effect of the processing described in FIG. 5 and FIG. 6;

FIG. 10 is a fourth explanatory diagram illustrating the effect of the processing described in FIG. 5 and FIG. 6;

FIG. 11 is a fifth explanatory diagram illustrating the effect of the processing described in FIG. 5 and FIG. 6;

FIG. 12 is a sixth explanatory diagram illustrating the effect of the processing described in FIG. 5 and FIG. 6;

FIG. 13 is a seventh explanatory diagram illustrating the effect of the processing described in FIG. 5 and FIG. 6;

FIG. 14 is an eighth explanatory diagram illustrating the effect of the processing described in FIG. 5 and FIG. 6;

FIG. 15 is a ninth explanatory diagram illustrating the effect of the processing described in FIG. 5 and FIG. 6;

FIG. 16 is a tenth explanatory diagram illustrating the effect of the processing described in FIG. 5 and FIG. 6;

FIG. 17 shows the outward form of an encapsulated endoscope system;

FIG. 18 is a block diagram showing the configuration of the encapsulated endoscope system shown in FIG. 17;

FIG. 19 is a block diagram showing the configuration of an encapsulated endoscope system;

FIG. 20 shows an example of a movement to be made by an encapsulated endoscope included in the system shown in FIG. 19;

FIG. 21 describes a flow of jiggling performed in the encapsulated endoscope system shown in FIG. 19;

FIG. 22 is an explanatory diagram showing the effect of the processing described in FIG. 21;

FIG. 23 is a block diagram showing the configuration of an encapsulated endoscope system;

FIG. 24 is a block diagram showing the configuration of an X-axis magnetic field generating unit included in the system shown in FIG. 23;

FIG. 25 is a first diagram showing the operation of the encapsulated endoscope system shown in FIG. 23; and FIG. 26 is a second diagram showing the operation of the encapsulated endoscope system shown in FIG. 23.

DETAILED DESCRIPTION OF THE PREFERRED EMBODIMENTS

First Embodiment (Constituent Features)

Figure 1:
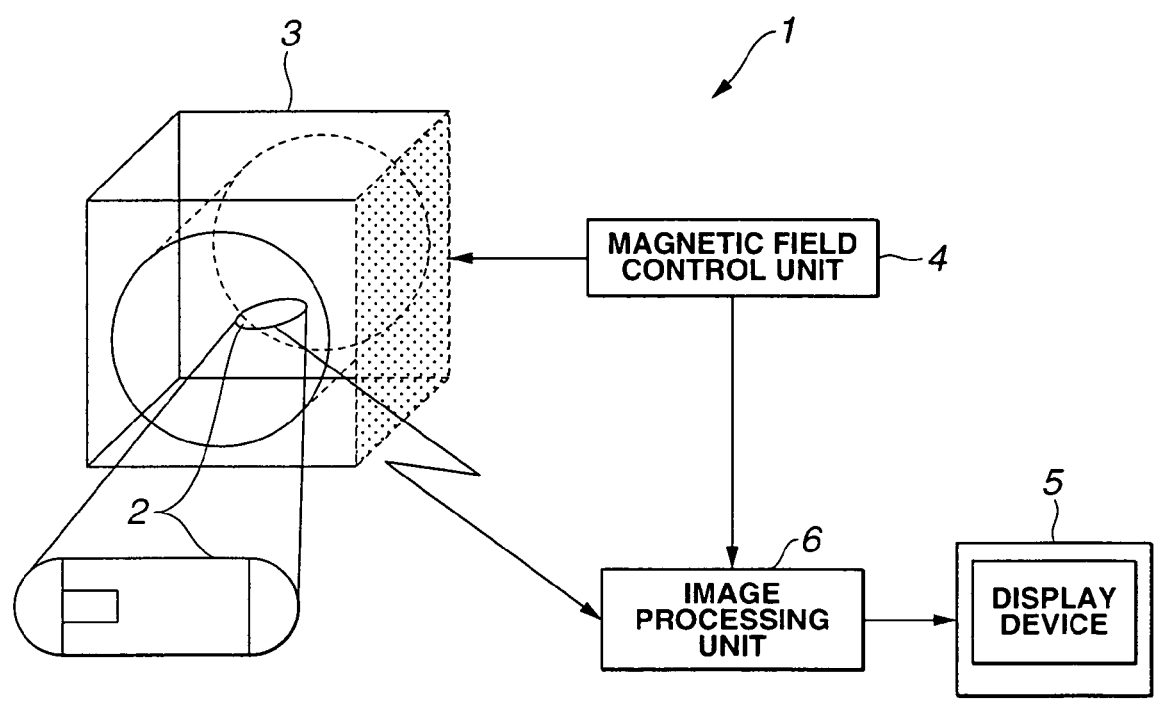

As shown in FIG. 1, an encapsulated endoscope system 1 in accordance with the present embodiment comprises: an encapsulated endoscope 2 that is inserted into a body cavity, moves by itself owing to an external rotating magnetic field, and picks up an image of the interior of a body cavity; a rotating magnetic field generating unit 3 that generates the external rotating magnetic field; a magnetic field control unit 4 that controls the rotating magnetic field generated by the rotating magnetic field generating unit 3; and an image processing unit 6 that receives a magnetic field control signal sent from the magnetic field control unit 4, receives an image from the encapsulated endoscope 2 by radio, performs image processing, and displays an image on a display device 5.

Figure 2:
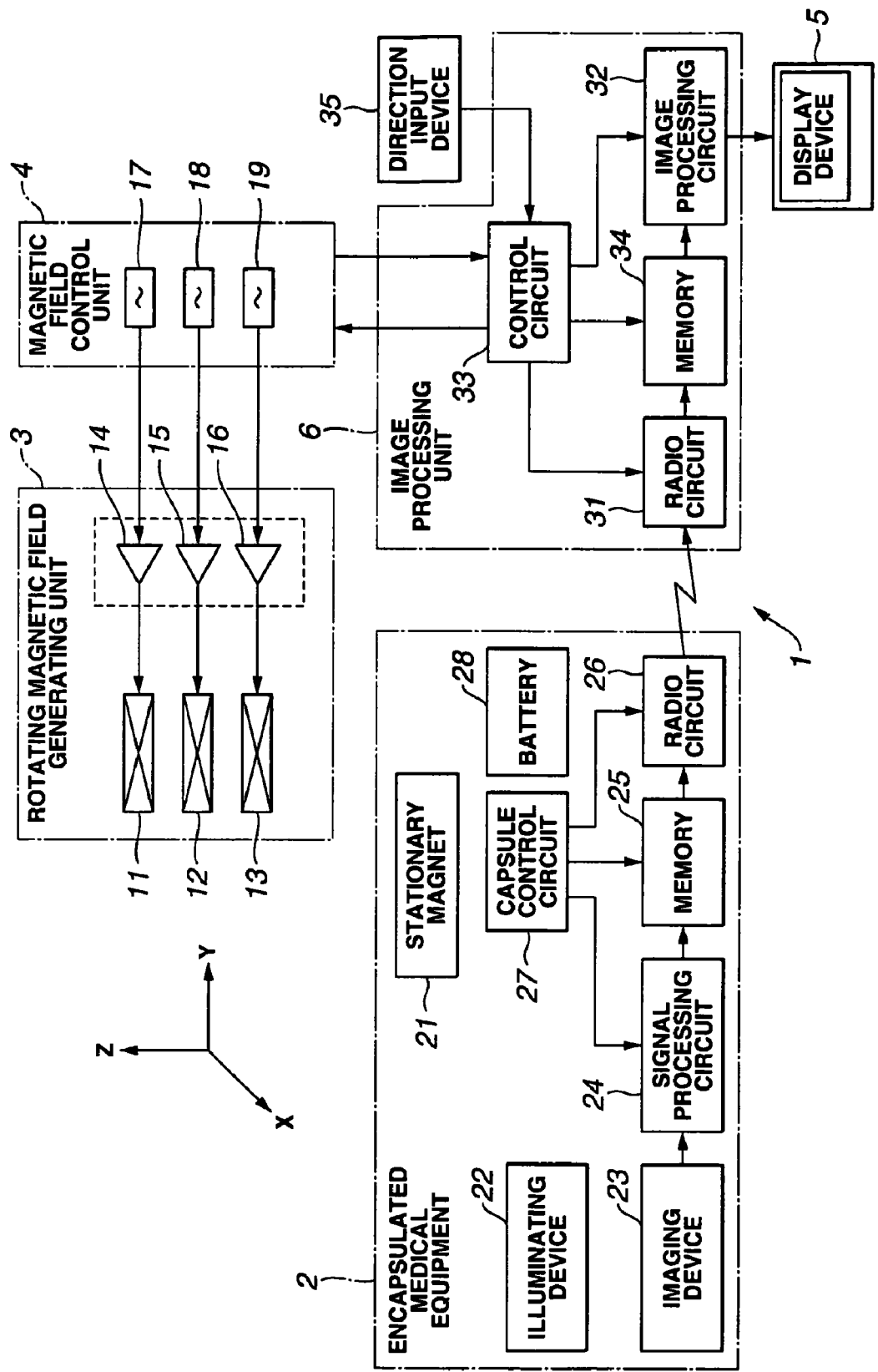

As shown in FIG. 2, the rotating magnetic field generating unit 3 comprises: a first electromagnet 11 that generates a magnetic field in an X-axis direction; a second electromagnet 12 that generates a magnetic field in a Y-axis direction; a third electromagnet 13 that generates a magnetic field in a Z-axis direction; and driving amplifiers 14 to 16 that drive the first to third electromagnets 11 to 13 respectively. The magnetic field control unit 4 is composed of control signal generators 17 to 19. The control signal generators 17 to 19 control the driving amplifiers 14 to 16 respectively, transmit a magnetic field control signal, in response to which the rotating magnetic field generating unit 3 generates a rotating magnetic field, to the rotating magnetic field generating unit 3, and transmit data of a magnetic field generated by the rotating magnetic field generating unit 3 to the image processing unit 6.

Incorporated in the encapsulated endoscope 2 are: a stationary magnet 21 that rotates while reacting to a rotating magnetic field; an illuminating device (for example, an LED) 22 that generates illumination light with which the interior of a body cavity is illuminated; an imaging device (for example, a CCD) 23 that images an intracavitary region illuminated with the illumination light; a signal processing circuit 24 that samples an image signal produced by the imaging device and converts it into a digital video signal; a memory 25 in which the digital video signal sent from the signal processing circuit 24 is stored; a radio circuit 26 that transmits the digital video signal stored in the memory 25 to the image processing unit 6 by radio; a capsule control circuit 27 for controlling the signal processing circuit 24, memory 25, and radio circuit 26; and a battery 28 that supplies power to the circuits incorporated in a capsule.

The image processing unit 6 comprises: a radio circuit 31 that receives image data sent from the encapsulated endoscope 2 by radio; a memory 34 in which a digital video signal received by the radio circuit 31 is stored as image data; an image processing circuit 32 that performs turning and other desired processing on the image data stored in the memory 34; and a control circuit 33 that receives data of a magnetic field generated by the rotating magnetic field generating unit 3 and controls the image processing circuit 32 and radio circuit 31. In the memory 34, the control circuit 33 stores the magnetic field data received from the magnetic field control unit 4 in association with image data.

Moreover, the control circuit 33 transmits an advancement control signal to the magnetic field control unit 4. The advancement control signal is produced based on an instruction signal received from a direction instructing device 35, for example, a keyboard or a joystick that is used to instruct a direction of advancement in which the encapsulated endoscope 2 should be advanced.

An operator determines a direction, in which the encapsulated endoscope 2 should be advanced, by monitoring an endoscopic image displayed on the display device 5. The operator handles the direction instructing device 35 in order to transmit an instruction signal to the control circuit 33. In response to the instruction signal, the control circuit 33 transmits an advancement control signal to the magnetic field control unit 4. The advancement control signal enables generation of a rotating magnetic field that causes the encapsulated endoscope 2 to change the orientation thereof or to advance.

Figure 3:
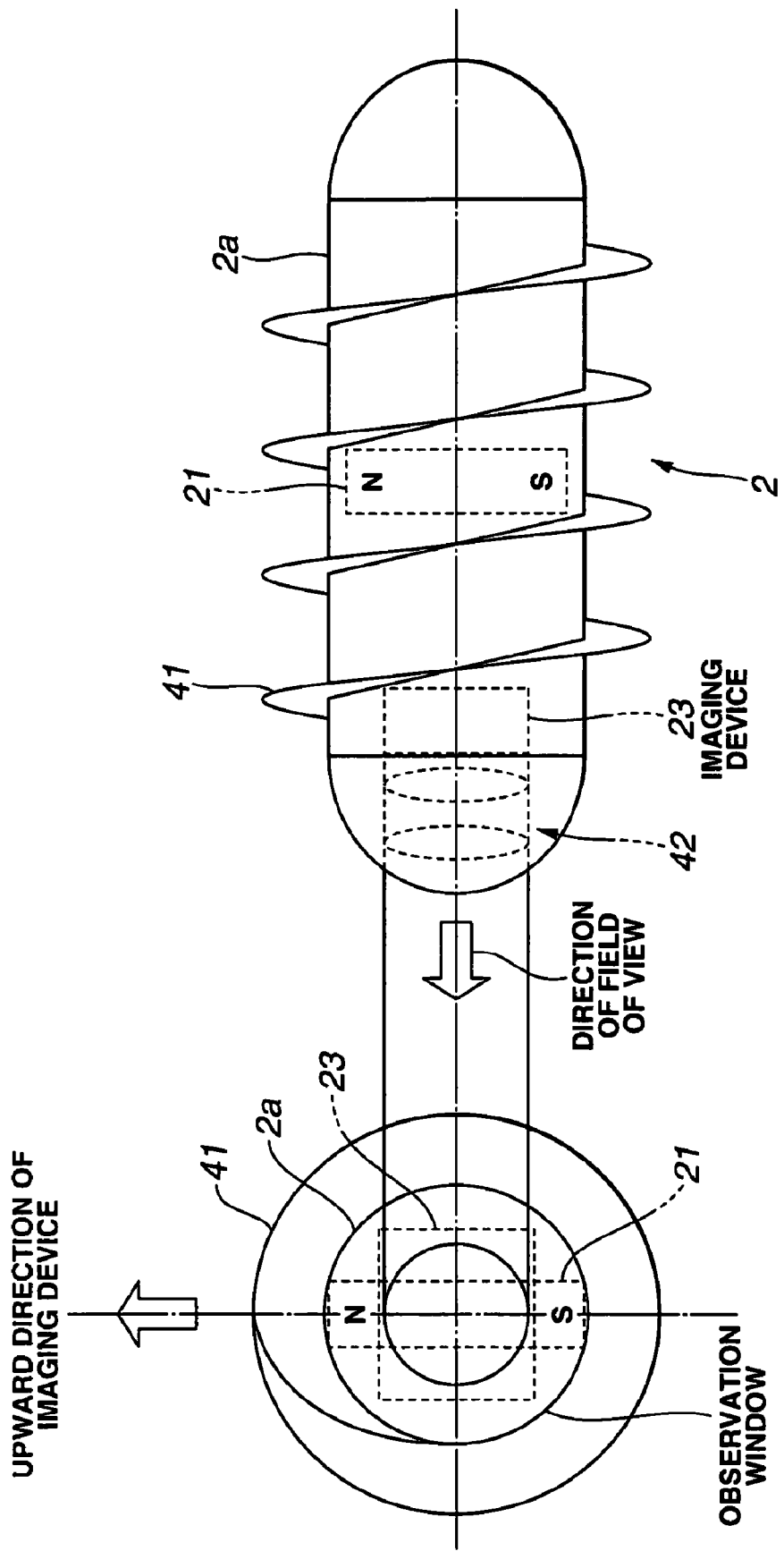

A capsule body 2a included in the encapsulated endoscope 2 is, as shown in FIG. 3, shaped like a capsule which a patient can gulp easily. The capsule body 2a has a screw 41 threaded helically on the periphery thereof. The imaging device 23 that images the interior of a body cavity via an objective optical system 42 is incorporated in one side of the capsule body 2a. The stationary magnet 21 is locked in the center part of the capsule body 2a. The stationary magnet 21 is locked to have a north pole thereof located in the upper part of the imaging surface of the imaging device 23 and a south pole thereof located in the lower part thereof.

A dipole of the stationary magnet 21 is located perpendicularly to the axis of rotation of the screw 41. The axis of rotation of the screw 41 is aligned with the axis of an imaging optical system ahead of the imaging device 23.

Incidentally, the orientations of the magnetic poles of the stationary magnet 21 are agreed with the upward and downward directions of the imaging surface of the imaging device 23. The present invention is not limited to this mode. The stationary magnet 21 and imaging device 23 should merely be locked in the capsule so that the imaging device 23 will rotate along with the rotation of the stationary magnet 21.

Figure 4:
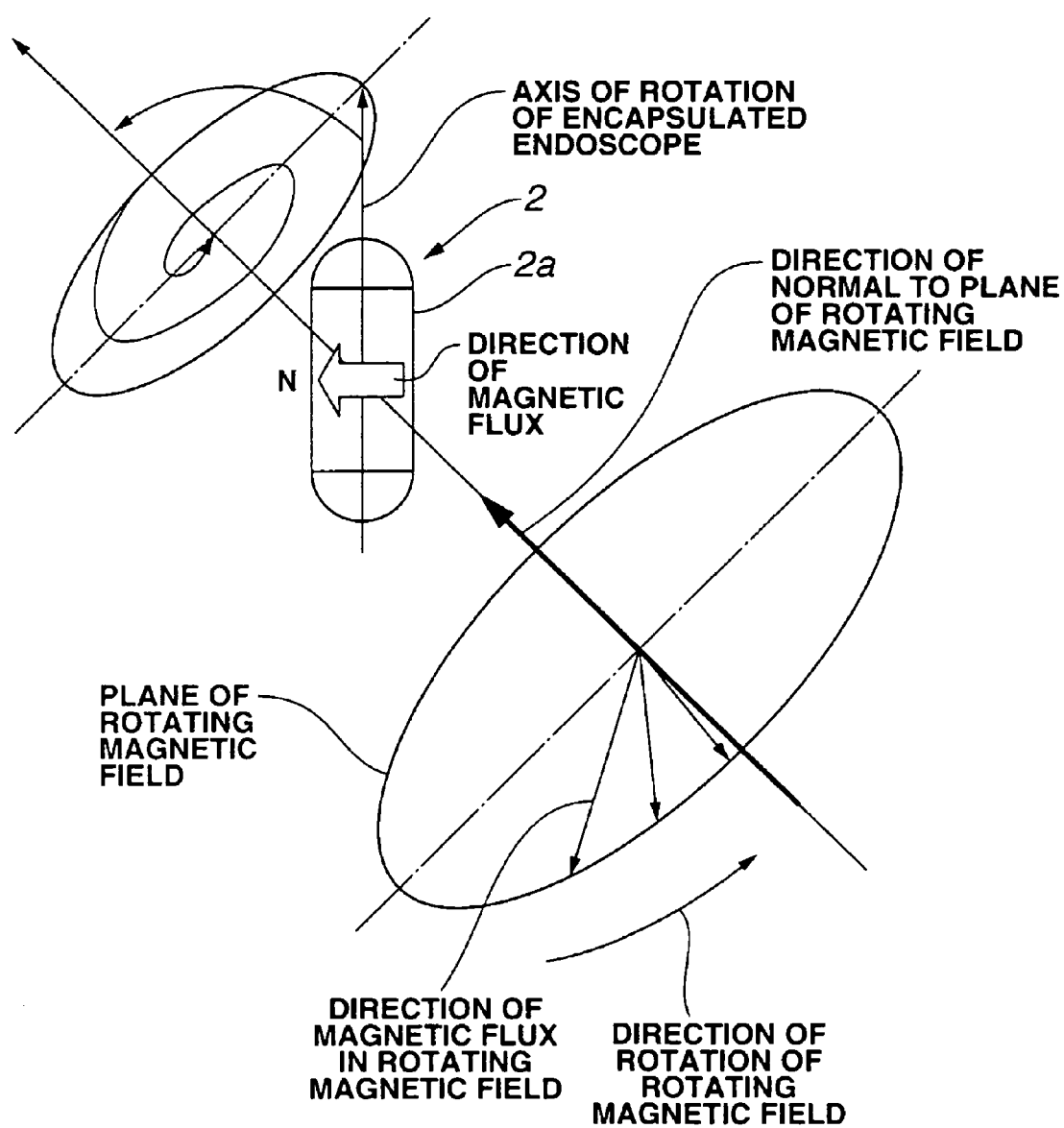

As shown in FIG. 4, when the encapsulated endoscope 2 is put in a body cavity, even if the axial direction of an observation optical system is not aligned with the direction of a normal to a rotating magnetic field, the rotating magnetic field acts on the stationary magnet 21. This causes the capsule body 2a to make a helical motion. Eventually, the axial direction of the observation optical system is aligned with the direction of the normal to the rotating magnetic field. In short, the rotating magnetic field acts on the stationary magnet 21 incorporated in the capsule body 2a so that the rotation of the stationary magnet 21 will be flush with the rotation of the rotating magnetic field. When the rotation of the stationary magnet 21 becomes flush with the rotation of the rotating magnetic field, the screw 41 comes in contact with a humor or an intracavitary wall due to the rotation of the stationary magnet 21 caused by the rotating magnetic field. This enables the encapsulated endoscope 2 to advance or withdraw in the direction of the normal to the plane of rotation of the rotating magnetic field.

A user monitors an endoscopic image displayed on the display device 5, and uses the direction instructing device 35 to instruct a desired direction. Consequently, as mentioned above, the direction of the normal to the rotating magnetic field can be changed to the desired direction. Eventually, the axial direction of the imaging optical system incorporated in the encapsulated endoscope 2 can be aligned with the desired direction. When the rotating magnetic field is rotated with the direction of the normal fixed, the encapsulated endoscope 2 can be advanced or withdrawn along the axis of the imaging optical system. The user can move the encapsulated endoscope 2 in any direction using the direction instructing device 35.

(Operation)

The operation of the present embodiment having the foregoing components will be described in conjunction with the flowcharts of FIG. 5 and FIG. 6 and the explanatory diagrams of FIG. 7 to FIG. 16.

When the orientation of the encapsulated endoscope 2 is changed or the encapsulated endoscope 2 is advanced or withdrawn, the imaging device 23 rotates together with the stationary magnet 21. An image picked up by the imaging device 23 also rotates. If the image is displayed on the display device 5 as it is, the displayed endoscopic image is a rotating image. The rotation of a display image must be ceased for fear that advancement or withdrawal in a desired direction may not be able to be instructed using the direction instructing device 35. According to the present embodiment, therefore, a rotating image is corrected to produce a still image.

First, when the direction instructing device 35 is handled, the encapsulated endoscope 2 picks up images time-sequentially, and stores a digital video signal in the memory 25. Under the control of the control circuit 33 included in the image processing unit 6, the digital video signal is stored in the memory 34 as image data via the radio circuits 26 and 31.

At this time, the control circuit 33 in the image processing unit 6 stores magnetic field data in association with the image data to be stored in the memory 34. The magnetic field data includes the orientation of a rotating magnetic field and the direction of the normal to the rotating magnetic field that are detected when the image data is produced. Consequently, a plurality of image data items, that is, first image data, second image data, etc., and n-th image data are, as shown in FIG. 7, successively stored in the memory 34. Moreover, a plurality of magnetic field data items, that is, first magnetic field data, second magnetic field data, etc., and n-th magnetic field data that are associated with the image data items are, as shown in FIG. 8, successively stored in the memory 34.

Figure 5:
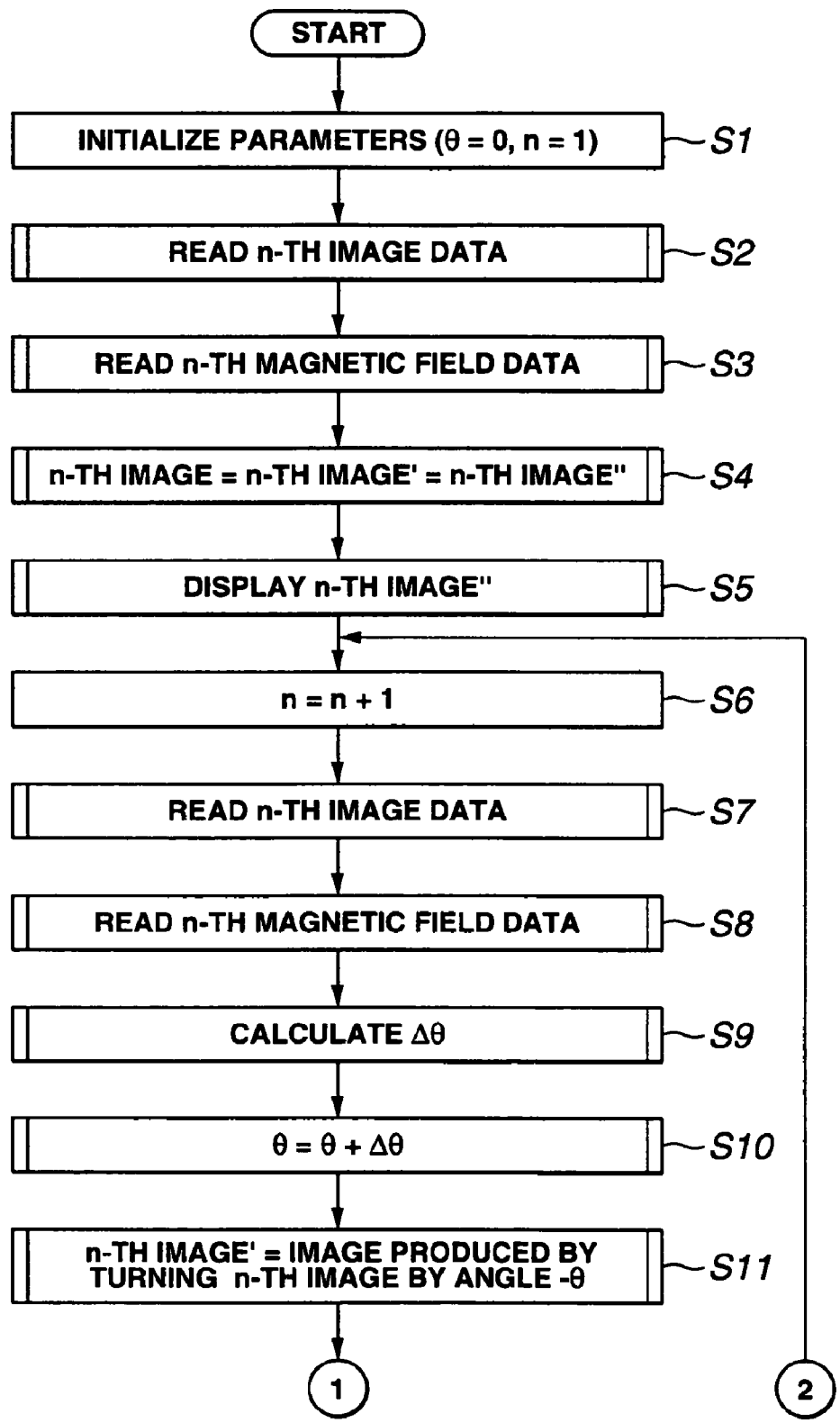

As described in FIG. 5, at step S1, the control circuit 33 in the image processing unit 6 initializes such parameters as a total angle of rotation of an image θ and an image number n to 0 and 1 respectively. At step S2, the control circuit 33 reads the n-th image data from the memory 34 (in this case, the first image data). At step S3, the n-th magnetic field data (in this case, the first magnetic field data) including the orientation of a rotating magnetic field (x, y, z) and the direction of the normal to the rotating magnetic field (X, Y, Z) detected at this time is read from the memory 34.

Figure 9:
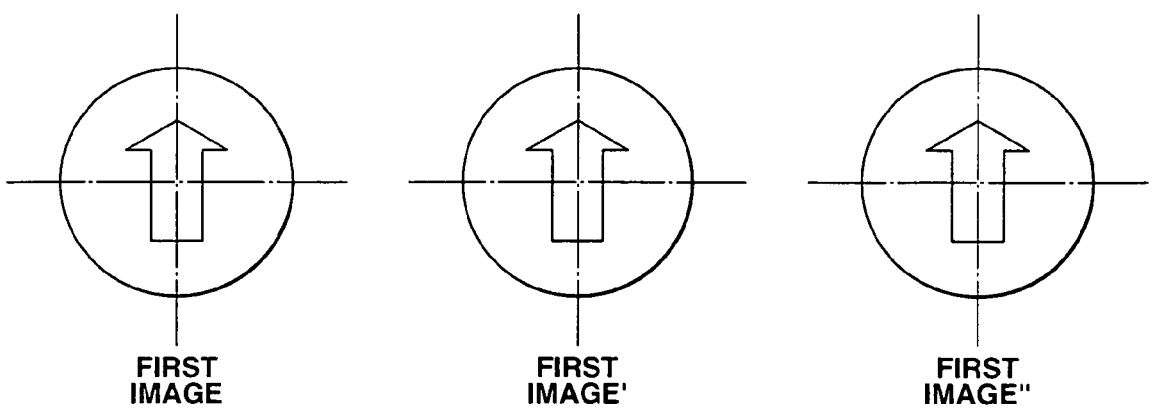
Figure 10:
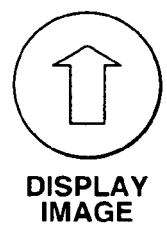

Thereafter, at step S4, the control circuit 33 adopts n-th image data' that is first corrected image data and n-th image data" that is second corrected image data as image data items identical to the n-th image data (n-th image data=n-th image data'=n-th image data": in FIG. 9, first image data=first image data'=first image data"). At step S5, the control circuit 33 controls the image processing circuit 32 to display a display image shown in FIG. 10 on the display device 5 according to the n-th image data".

Thereafter, at step S6, the control circuit 33 increments the image number n. At step S7, the n-th image data (in this case, second image data) is read from the memory 34. At step S8, the n-th magnetic field data (in this case, second magnetic field data) including the orientation of a rotating magnetic field (x, y, z) and the direction of the normal to the rotating magnetic field (X, Y, Z) detected at this time is read from the memory 34.

Thereafter, at step S9, the control circuit 33 calculates an angle of rotation $\Delta\theta$ by which the n−1-th image has rotated relative to the n-th image. The details will be presented below in conjunction with FIG. 11. For example, the orientation of a rotating magnetic field included in the first magnetic field data concerning the first image data shall be B1(x1,y1,z1), the direction of the normal to the rotating magnetic field included therein shall be R1(X1,Y1,Z1), the orientation of a rotating magnetic field included in the second magnetic field data concerning the second image data shall be B2(x2,y2,z2), and the direction of the normal to the rotating magnetic field shall be R2(X2,Y2,Z2).

Figure 11:
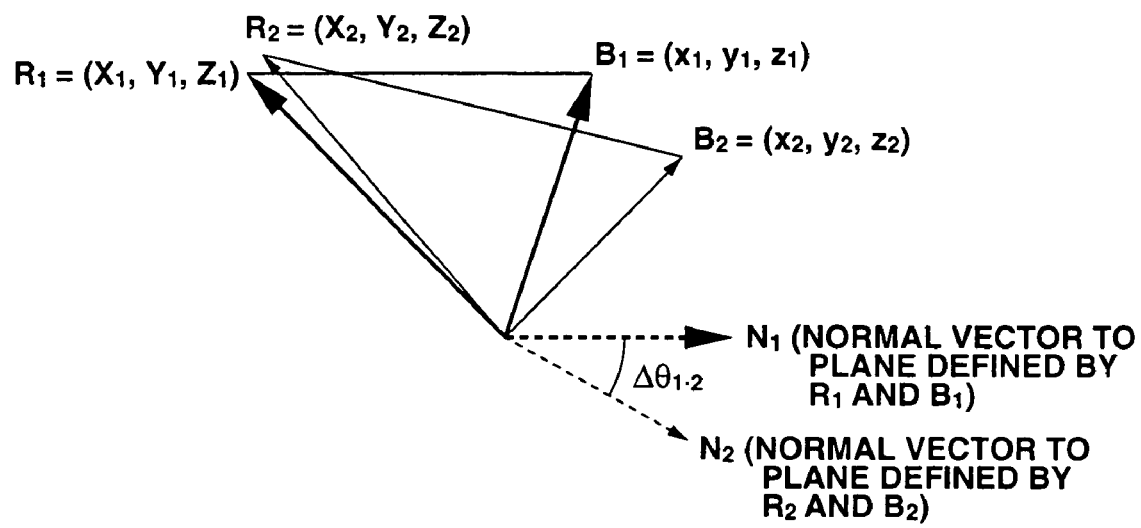

The direction of advancement of the encapsulated endoscope 2 varies time-sequentially. If an angle at which the orientation B1 meets the orientation B2 is regarded as an angle of rotation, there is a possibility that the angle of rotation may not agree with an actual angle of rotation. Therefore, as shown in FIG. 11, an angle at which a normal vector N1 to a plane defined by the orientation R1 and direction B1 meets a normal vector N2 to a plane defined by the orientation R2 and direction B2 is regarded as the angle of rotation $\Delta\theta$.

The angle of rotation $\Delta\theta$ is calculated as follows:

$$N1=(y1Z1-Y1z1, z1X1-Z1x1, x1Y1-X1y1)$$

$$N2=(y2Z2-Y2z2, z2X2-Z2x2, x2Y2-X2y2)$$

where N1 and N2 denote unit vectors;

$$\Delta\theta^{1\cdot 2}=\cos^{-1}\{(y1Z1-Y1z1)(y2Z2-Y2z2)\}$$

With the elapse of time, the angles of rotation $\Delta\theta^{1\cdot 2}$, $\Delta\theta^{2\cdot 3}$, etc., $\Delta\theta^{(n-2)\cdot(n-1)}$, and $\Delta\theta^{(n-1)\cdot n}$ are calculated successively.

Figure 12:
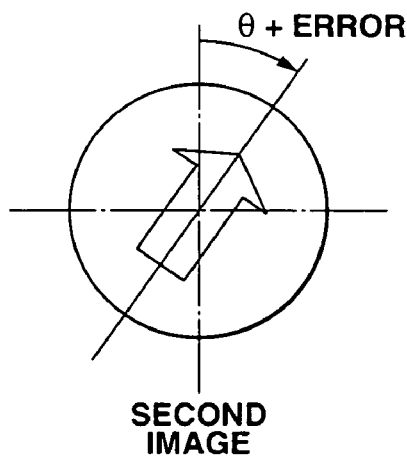

A total angle of rotation θ is calculated as the sum total of the angles of rotation and expressed as $\theta=\Sigma\Delta\theta^{(k-1)\cdot k}$. At step S10, the control circuit 33 calculates the total angle of rotation as θ=θ+Δθ. As shown in FIG. 12, for example, the second image is an image that has rotated relative to the first image by the angle of rotation θ plus an error in an illustrated direction. Herein, the error is an error between the angle of rotation of the encapsulated endoscope 2 and the angle of rotation of the rotating magnetic field deriving from a load which an intracavitary wall imposes on the screw 41 threaded on the rotating encapsulated endoscope 2.

Figure 13:
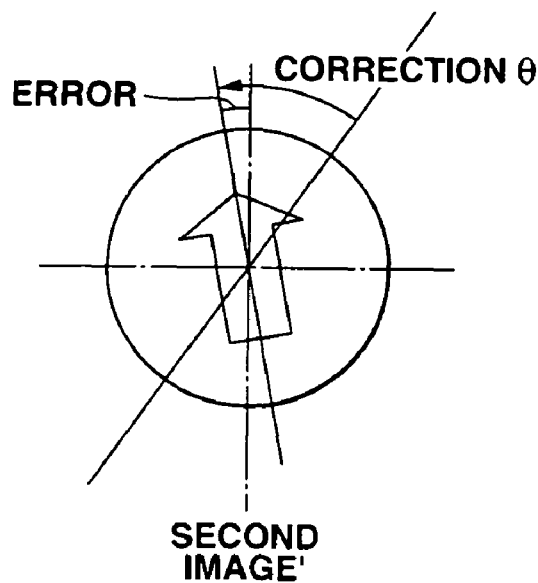

At step S11, the control circuit 33 adopts the n-th image data' that is the first corrected image data as image data that has rotated by an angle −θ relative to the n-th image data. Consequently, as shown in FIG. 13, for example, the second image' that is the first corrected image is produced with no consideration taken into the error.

Figure 6:
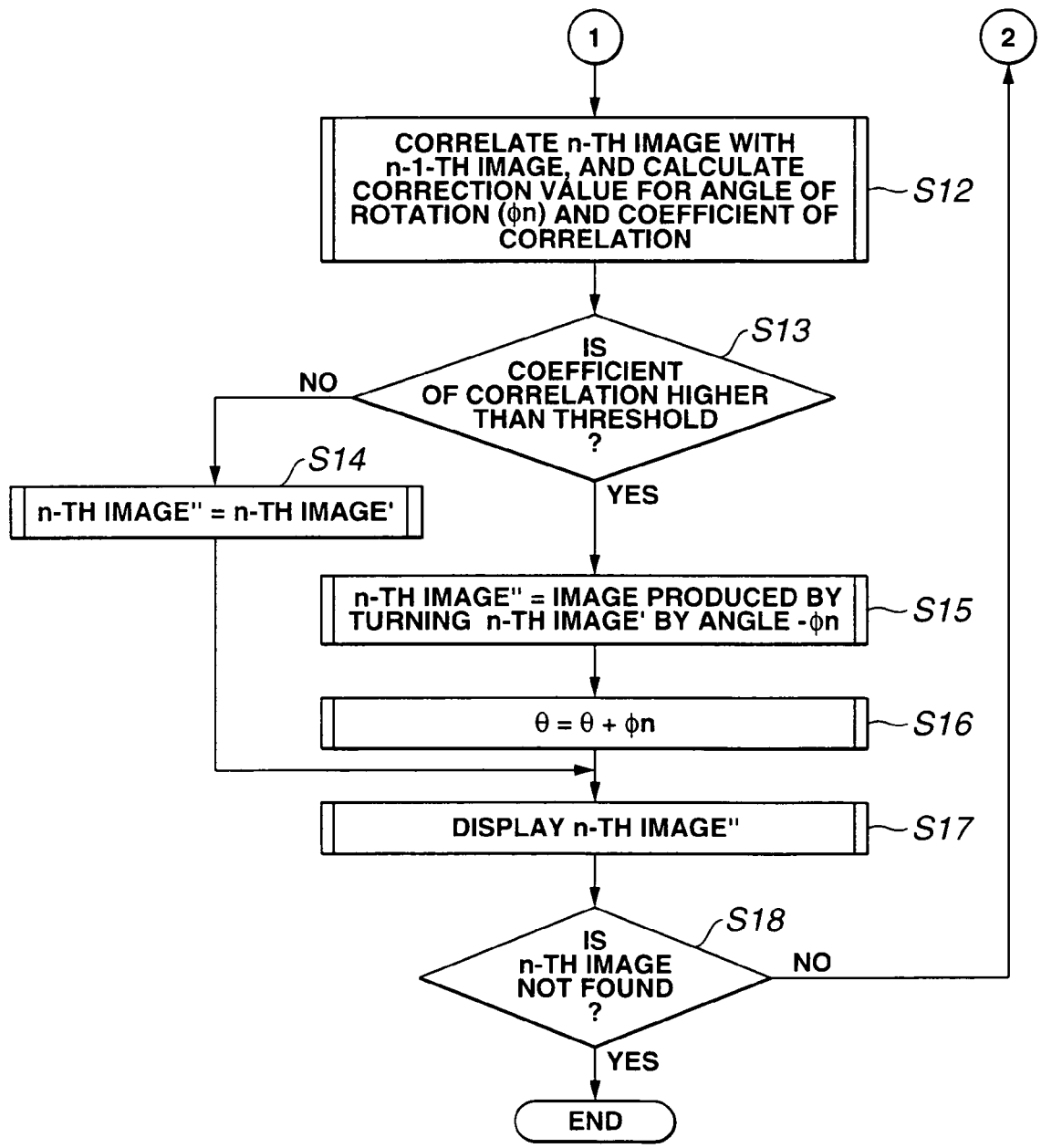

Control is then passed to step S12 described in FIG. 6. At step S12, the control circuit 33 correlates the n-th image data with the n-1-th image data according to a known procedure, and calculates a degree of correction (φn) to which an angle of rotation should be corrected and a coefficient of correlation. At step S13, the control circuit 33 verifies whether the coefficient of correlation exceeds a predetermined threshold value. Based on the result of the verification, it is verified whether the error shown in FIG. 12 is ignored.

If the coefficient of correlation does not exceed the predetermined threshold value, at step S14, the control circuit 33 adopts the n-th image data", which is the second corrected image data, as the n-th image data' that is the first corrected image data, and passes control to step S17. If the coefficient of correlation does not exceed the predetermined threshold value, it signifies that an image has changed greatly. In this case, the result of correlation is not adopted. When step S11 is completed (the n-th image data' that is the first corrected image data is adopted as image data that has rotated by an angle −θ relative to the n-th image data), rotational correction of an image is completed.

Figure 14:
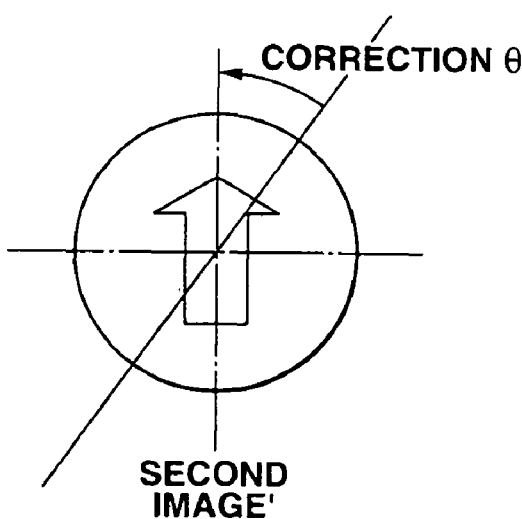

If the error can be ignored, as shown in FIG. 14, rotational correction of the second image data is completed by adopting the second image data' (first corrected image data) at step S11. At step S14, the second image data' (first corrected image data) is adopted as the second image data" (second corrected image data).

Figure 15:
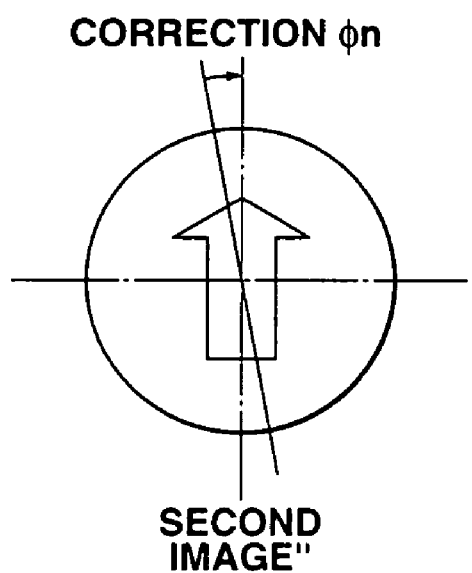

If the coefficient of correlation exceeds the predetermined threshold value, the control circuit 33 adopts at step S15 the n-th image data" that is the first corrected image data as image data that has rotated by an angle −φn relative to the n-th image data" that is the second corrected image data. Consequently, as shown in FIG. 15, the second image" that is the second corrected image is thus available. At step S16, the total angle of rotation θ is set to an angle θ+φn. Control is then passed to step S17.

Figure 16:
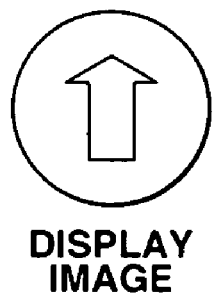

At step S17, the control circuit 33 controls the image processing circuit 33 so as to display, as shown in FIG. 16, a display image, which results from rotational correction achieved by adopting the n-th image data", on the display device 5. At step S18, the control circuit 33 verifies whether the n+1-th image data is found in the memory 34. If the n+1-th image data is found, control is returned to step S6 described in FIG. 5. If the n+1-th image data is unfound, processing is terminated.

When an image to be displayed on the image device 5 is an image having a round contour, the image can be displayed with a user left unconscious of rotation of the image.

(Advantages)

As mentioned above, according to the present embodiment, image data representing an image picked up by the encapsulated endoscope 2 can be stored in the memory 34 while being associated with magnetic field data detected during the picking up (the orientation of a rotating magnetic field and the direction of the normal thereto). By the way, the encapsulated endoscope 2 is rotated using a rotating magnetic field in order to thus change the orientation of the encapsulated endoscope 2 or advance or withdraw the encapsulated endoscope 2. Nevertheless, rotation of an image deriving from the rotation of the encapsulated endoscope 2 can be corrected by adopting the first corrected image.

Furthermore, the error between the angle of rotation of the encapsulated endoscope 2 and the angle of rotation of the rotating magnetic field deriving from a load an intracavitary wall imposes on the screw 41 on the rotating encapsulated endoscope 2 can be corrected by adopting the second corrected image through correlation of images.

Moreover, an image whose rotation is ceased can be displayed at a still image on the display device 5. A direction in which the encapsulated endoscope 2 should be moved can be identified easily from the image. Once the direction instructing device 35 is handled, the control circuit 33 receives an instruction signal from the direction instructing device 35, and transmits an advancement control signal based on the instruction signal to the magnetic field control unit 4. Consequently, the axial direction of the imaging optical system included in the encapsulated endoscope 2 can be set to a desired direction. Moreover, the encapsulated endoscope 2 can be advanced or withdrawn along the axis of the imaging optical system. A user uses the direction instructing device 35 to move the encapsulated endoscope 2 in any direction.

Second Embodiment

A second embodiment of the present invention is nearly identical to the first embodiment thereof. Only a difference will be described. The same reference numerals will be assigned to identical components, and the description of the components will be omitted.

(Constituent Features and Operation)

Figure 17:
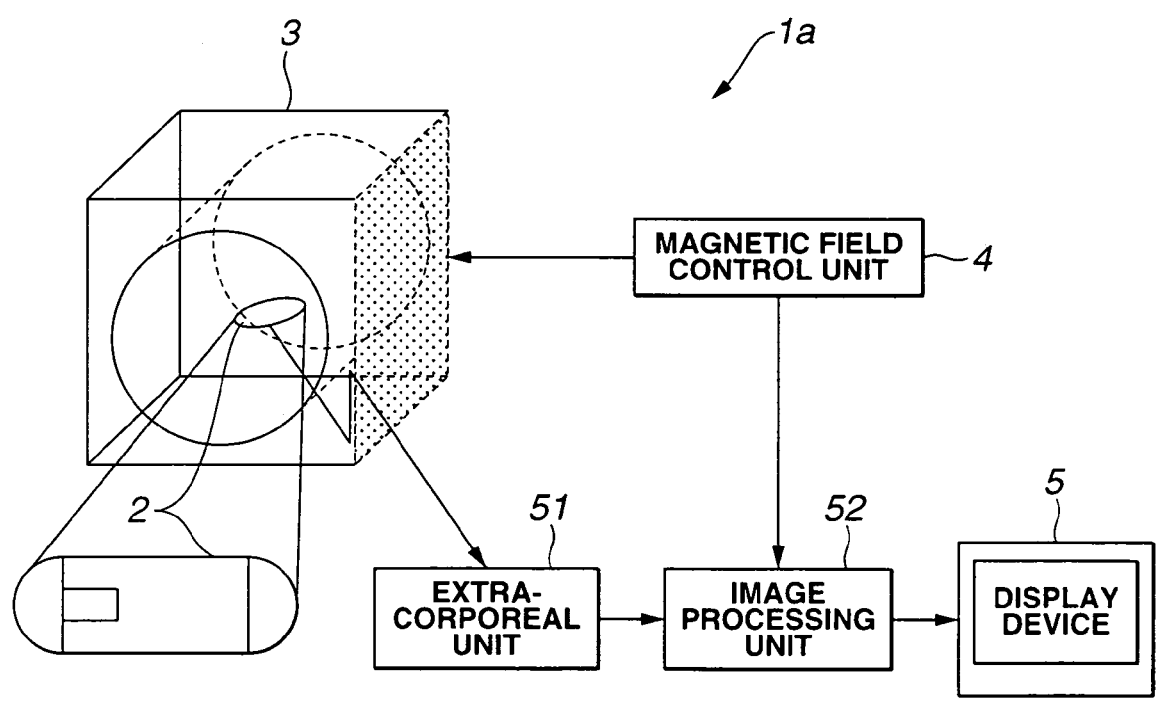
FIG. 17 and FIG. 18 are concerned with a second embodiment of the present invention.

As shown in FIG. 17, an encapsulated endoscope system 1a in accordance with the present embodiment comprises: an encapsulated endoscope 2 that is inserted into a body cavity and moves by itself owing to an external rotating magnetic field so as to pick up an image of the interior of a body cavity; a rotating magnetic field generating unit 3 that generates the external rotating magnetic field; a magnetic field control unit 4 that controls the rotating magnetic field generated by the rotating magnetic field generating unit 3; and an extracorporeal unit 51 that receives a magnetic field control signal from the magnetic field control unit 4, receives image data from the encapsulated endoscope 2 by radio, and stores the image data in association with magnetic field data in a memory. The extracorporeal unit 51 can transmit the image data and magnetic field data stored in the memory to an image processing unit 52 realized with a personal computer or the like.

Transferring data from the extracorporeal unit 51 to the image processing unit 52 is achieved by, for example, connecting the extracorporeal unit 51 directly to the image processing unit 52 after the completion of an examination performed using the encapsulated endoscope 2. Otherwise, the data transfer may be achieved via an information recording medium that can be freely connected or disconnected (for example, a floppy disk drive, a magneto-optical drive, a CD-R drive, a CD-RW disk drive, a DVD-R disk drive, or the like). Otherwise, the data transfer may be achieved over a communication network such as an in-house LAN. The image processing unit 52 uses, similarly to the one included in the first embodiment, image data and magnetic field data to cease the rotation of an image so as to produce a still image and then displays the image on the display device 5.

Figure 18:
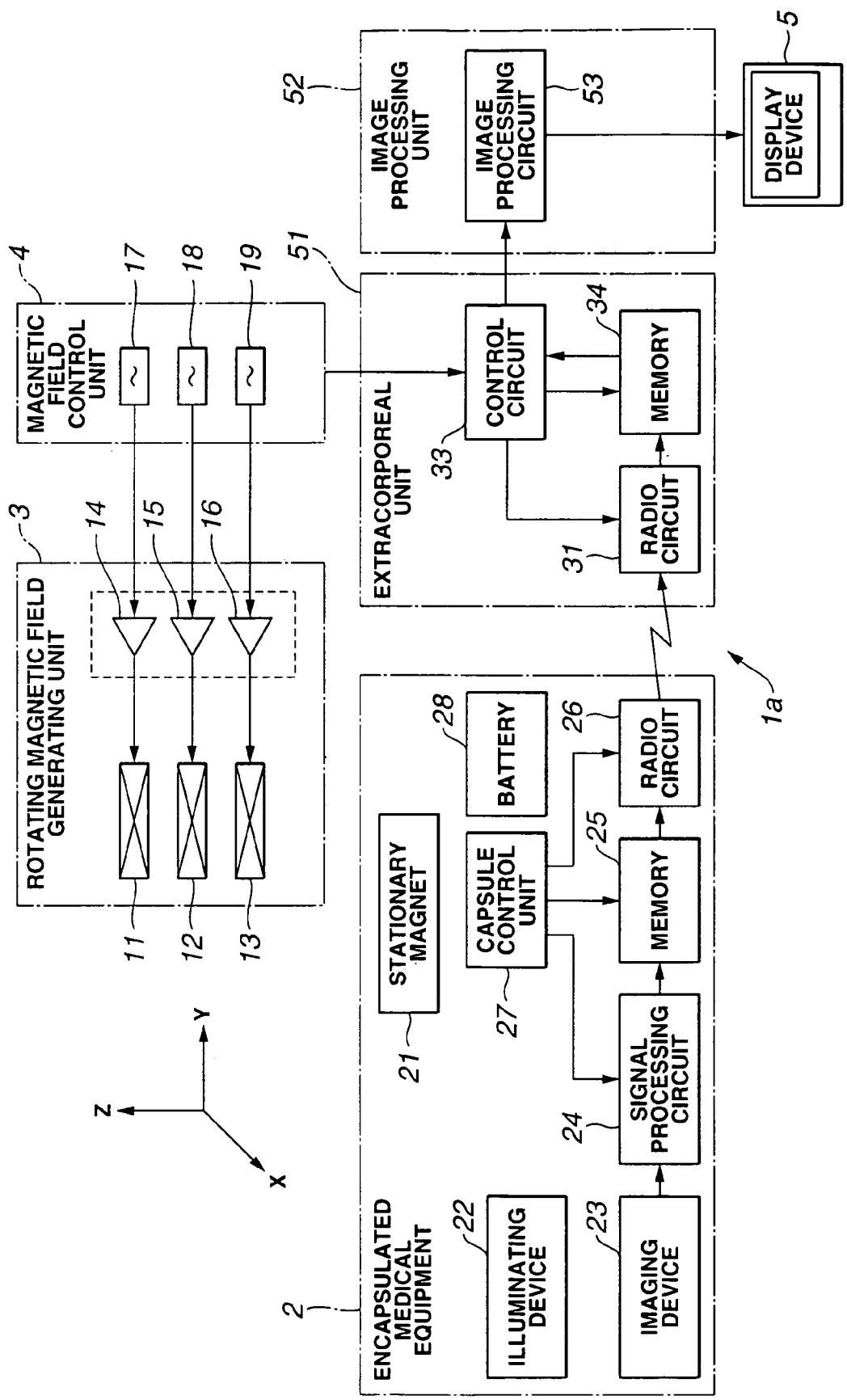

As shown in FIG. 18, the extracorporeal unit 51 includes a radio circuit 31, a memory 34, and a control circuit 33. In the memory 34, the control circuit 33 stores magnetic field data in association with image data.

The image processing unit 52 includes, similarly to the one included in the first embodiment, an image processing circuit 53 that uses image data and magnetic field data to cease the rotation of an image so as to produce a still image, then performs image processing, and displays the resultant image on the display device 5.

The other components of the second embodiment and the operation thereof are identical to those of the first embodiment.

(Advantages)

According to the present embodiment, similarly to the first embodiment, the encapsulated endoscope 2 is rotated using a rotating magnetic field in order to change the orientation of the encapsulated endoscope 2 or advance or withdraw the encapsulated endoscope 2. Nevertheless, the rotation of an image deriving from the rotation of the encapsulated endoscope 2 can be corrected by adopting the first corrected image. The error between the angle of rotation of the encapsulated endoscope 2 and the angle of rotation of the rotating magnetic field deriving from a load an intracavitary wall imposes on the screw 41 on the rotating encapsulated endoscope 2 can be corrected by adopting the second corrected image through correlation of images.

Furthermore, according to the present embodiment, when an examination is performed using the encapsulated endoscope 2, image data is stored in association with magnetic field data in the memory 34. Rotational correction is performed after the examination. The examination can therefore be performed efficiently. Moreover, the image processing unit 52 can be realized with a general-purpose personal computer. The encapsulated endoscope system 1a can be configured inexpensively.

Third Embodiment

A third embodiment of the present invention is nearly identical to the first embodiment thereof. Only a difference will be described. The same reference numerals will be assigned to identical components, and the description of the components will be omitted.

(Constituent Features)

Figure 19:
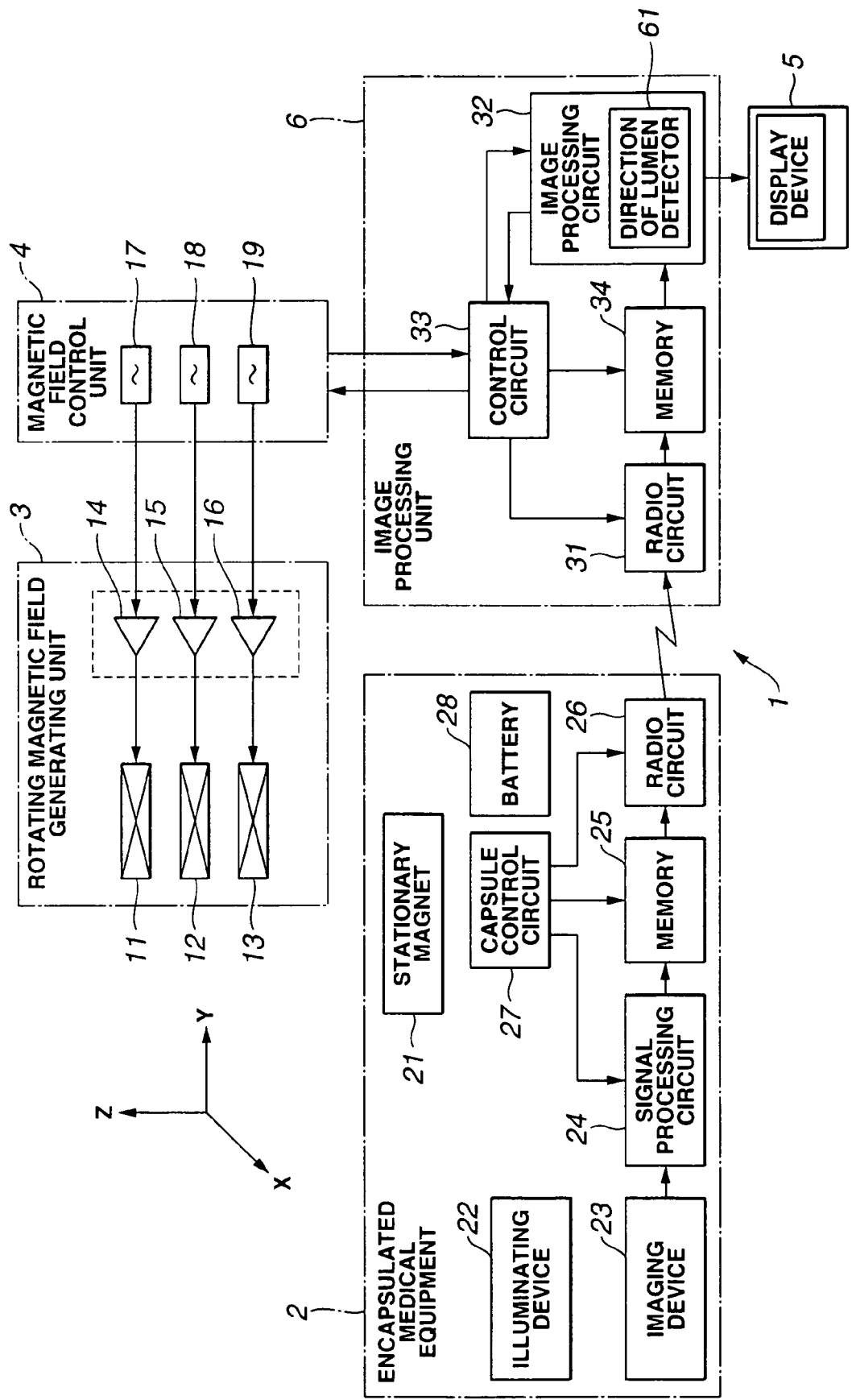
FIG. 19 to FIG. 22 are concerned with a third embodiment of the present invention.

As shown in FIG. 19, an image processing circuit 32a included in an image processing unit 6 in the present embodiment includes a direction-of-lumen detector 61 that detects the direction of a lumen using image data representing an image whose rotation is ceased. Since the direction-of-lumen detector 61 is included, the direction of a lumen is detected automatically without the use of the direction instructing device 35 included in the first embodiment. The encapsulated endoscope can then be advanced in order to pick up a view image.

When the direction-of-lumen detector 61 detects a distinct lumen present within a field of view, it is verified that the encapsulated endoscope keeps advancing in a rectilinear direction. If no lumen is detected within the field of view, the direction of advancement, that is, a direction in which a lumen extends is determined based on some information.

One of criterion for determining the direction of advancement when no lumen is detected within the field of view is a brightness changing direction in an image. For example, a change in brightness occurs widely from an area in an image depicting a portion of an encapsulated endoscope near the distal end thereof to an area therein depicting a portion thereof away from the distal end. In this case, the direction of advancement is a direction receding from the distal end of the encapsulated endoscope. Thus, an inserting direction can be detected by detecting a direction of a change from a light in an image to a dark therein.

The detailed configuration and operation of the direction-of-lumen detector 61 are identical to those of an inserting direction detecting unit described in Japanese Patent Application No. 2001-292230 filed by the present applicant. The description of the configuration and operation will therefore be omitted.

The other components are identical to those of the first embodiment.

(Operation)

Similarly to the first embodiment, the rotation of an image is ceased to produce a still image and the still image is displayed on the display device 5. Based on the image whose rotation is ceased, the direction-of-lumen detector 61 detects the direction of advancement of the encapsulated endoscope 2, and transmits an instruction signal to the control circuit 33 in the image processing unit 6. The control circuit 33 controls, similarly to the one included in the first embodiment, the magnetic field control unit 4 in response to the instruction signal, and then moves the encapsulated endoscope 2 in a direction in which a lumen extends.

Figure 20:
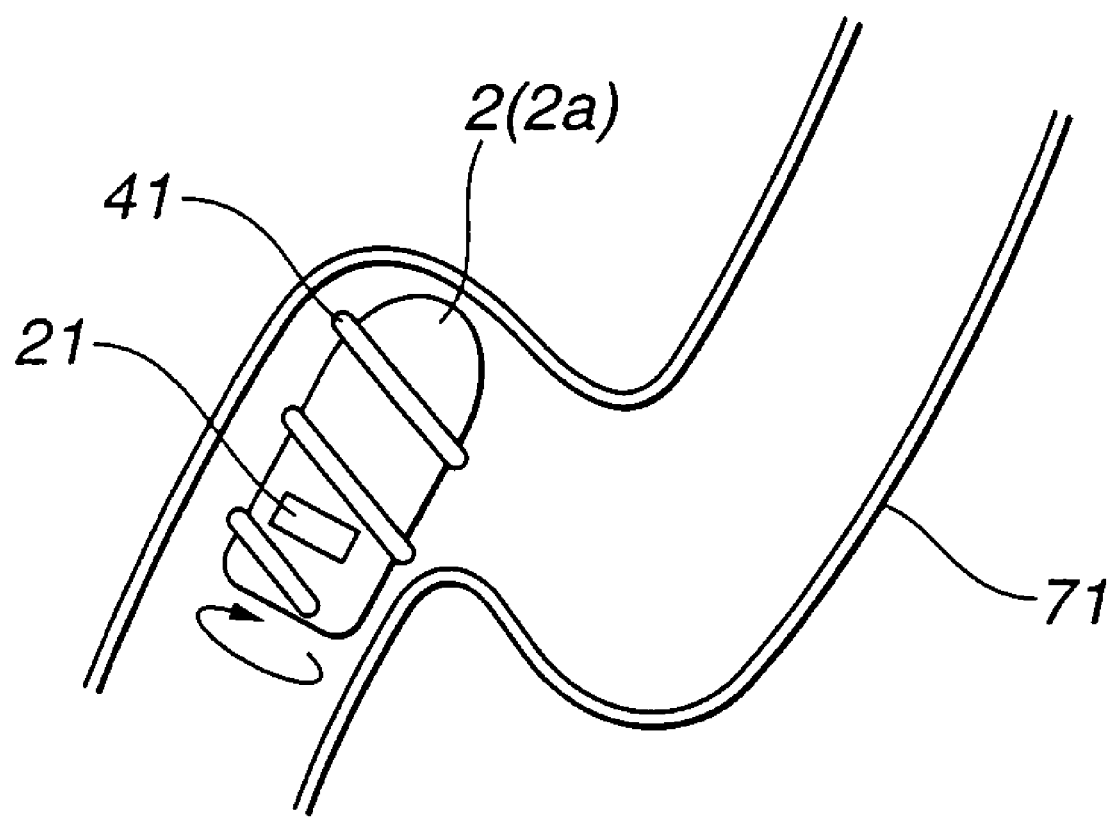

As shown in FIG. 20, for example, a lumen like an intestinal lumen 71 may have a small diameter and bend sharply, and the encapsulated endoscope 2 may not be able to advance because it cannot change its orientation. In this case, according to the present invention, the encapsulated endoscope 2 is jiggled as described below.

Figure 21:
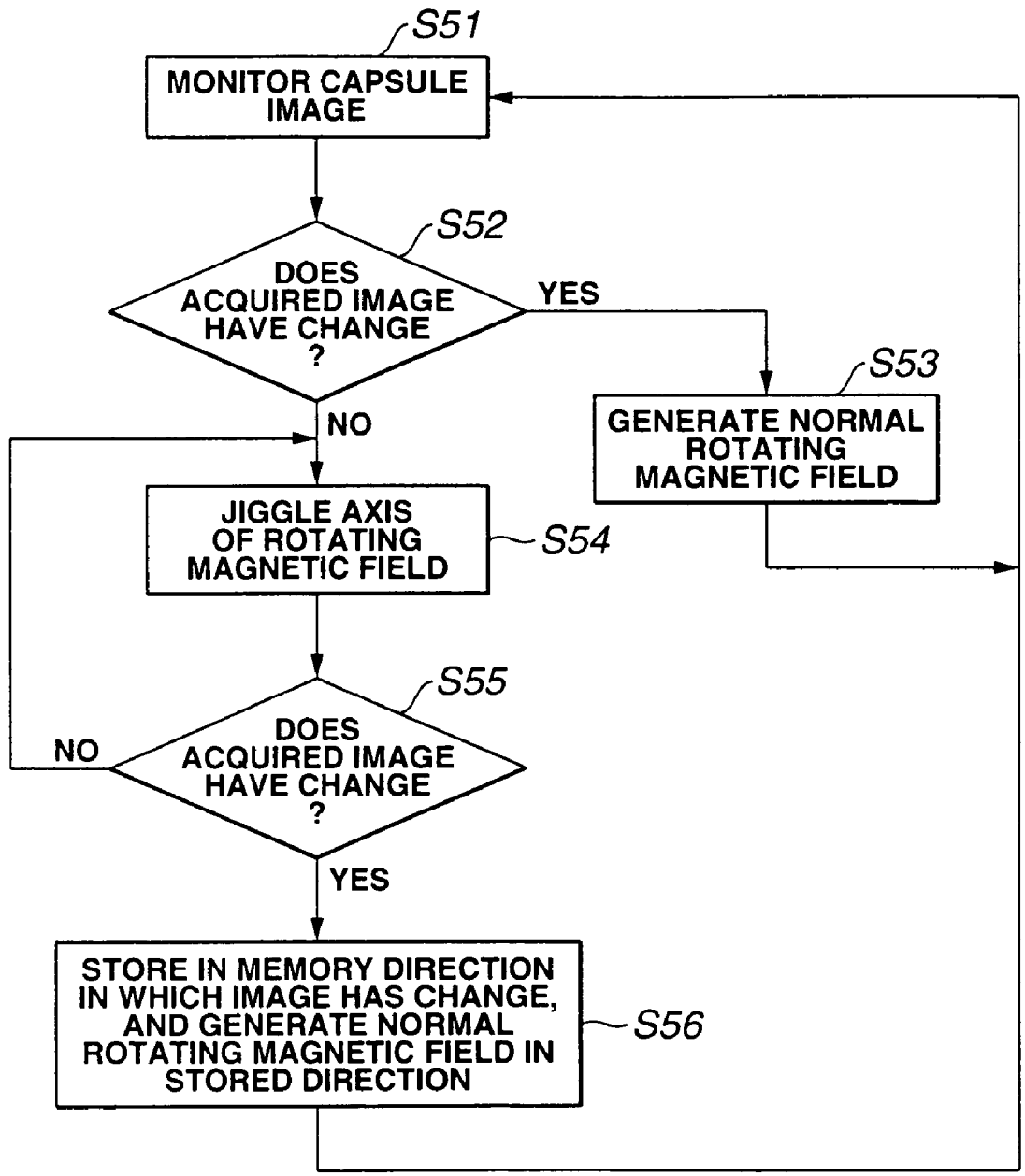

Specifically, as shown in FIG. 21, the control circuit 33 monitors an image, of which rotation is ceased, at step S51. At step S52, the image is correlated with a previous one in order to verify whether the image has changed. If the image has changed, a normal rotating magnetic field is generated at step S53 and control is returned to step S51. If the image has not changed, it is verified that the encapsulated endoscope 2 has failed to advance. Control is then passed to step S54.

Figure 22:
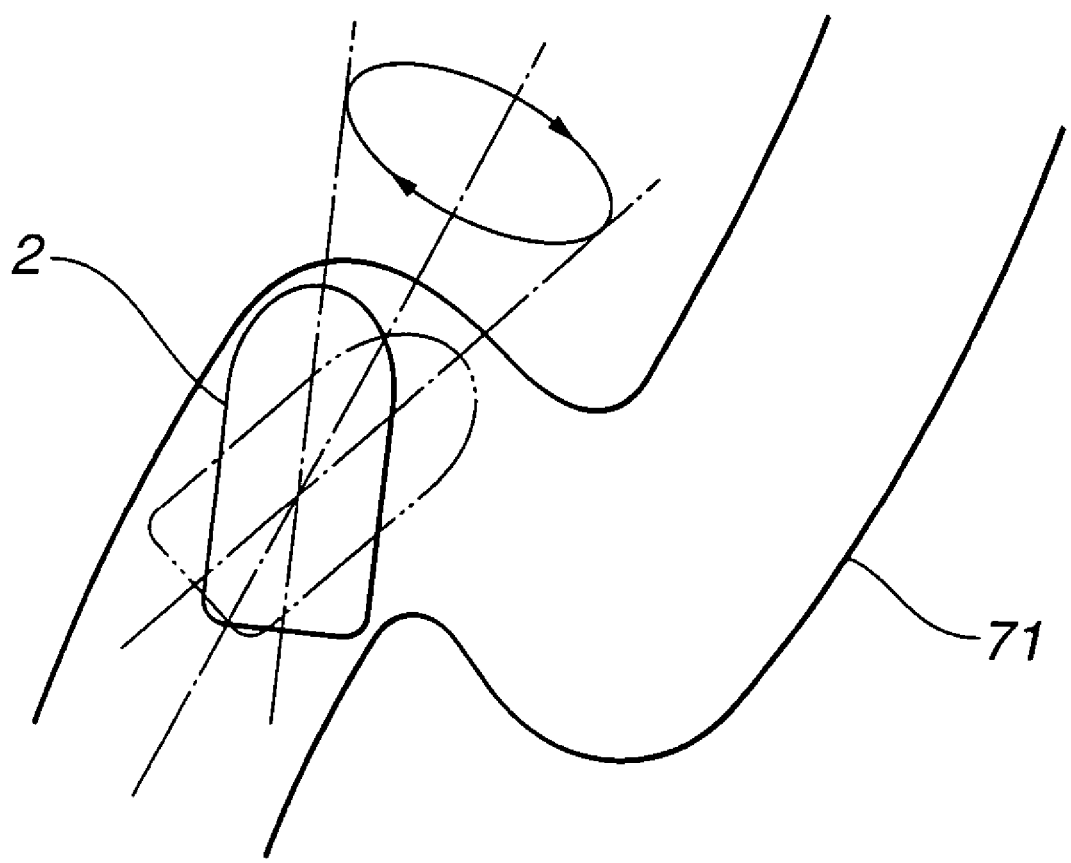

At step S54, the control circuit 33 controls and jiggles the axis of the rotating magnetic field as shown in FIG. 22. Specifically, for example, (1) the axis of the rotating magnetic field is moved conically, (2) the axis of the rotating magnetic field is simply swung from side to side, (3) the axis of the rotating magnetic field is simply vibrated with a short amplitude, or (4) the axis of the rotating magnetic field is simply shifted by 90°. Thus, the axis of the rotating magnetic field is jiggled in an attempt to free the stalled encapsulated endoscope 2.

At step S55, the control circuit 33 correlates the image with a previous one and verifies whether the image has changed. If the image has not changed, control is returned to step S54. If the image has changed, a direction in which the image has changed is stored in a memory. A normal rotating magnetic field is generated in the direction, and control is returned to step S51.

(Advantages)

As mentioned above, the present embodiment has the same advantages as the first embodiment. In addition, the direction of advancement of the encapsulated endoscope 2 can be verified and controlled. A user need not instruct a direction of advancement but can concentrate on observation. Moreover, since the encapsulated endoscope 2 is jiggled, the capability to pass through a narrow lumen can be improved greatly.

Fourth Embodiment

A fourth embodiment of the present invention is nearly identical to the first embodiment thereof. Only a difference will be described below. The same reference numerals will be assigned to identical components, and the description of the components will be omitted.

(Constituent Features)

Figure 23:
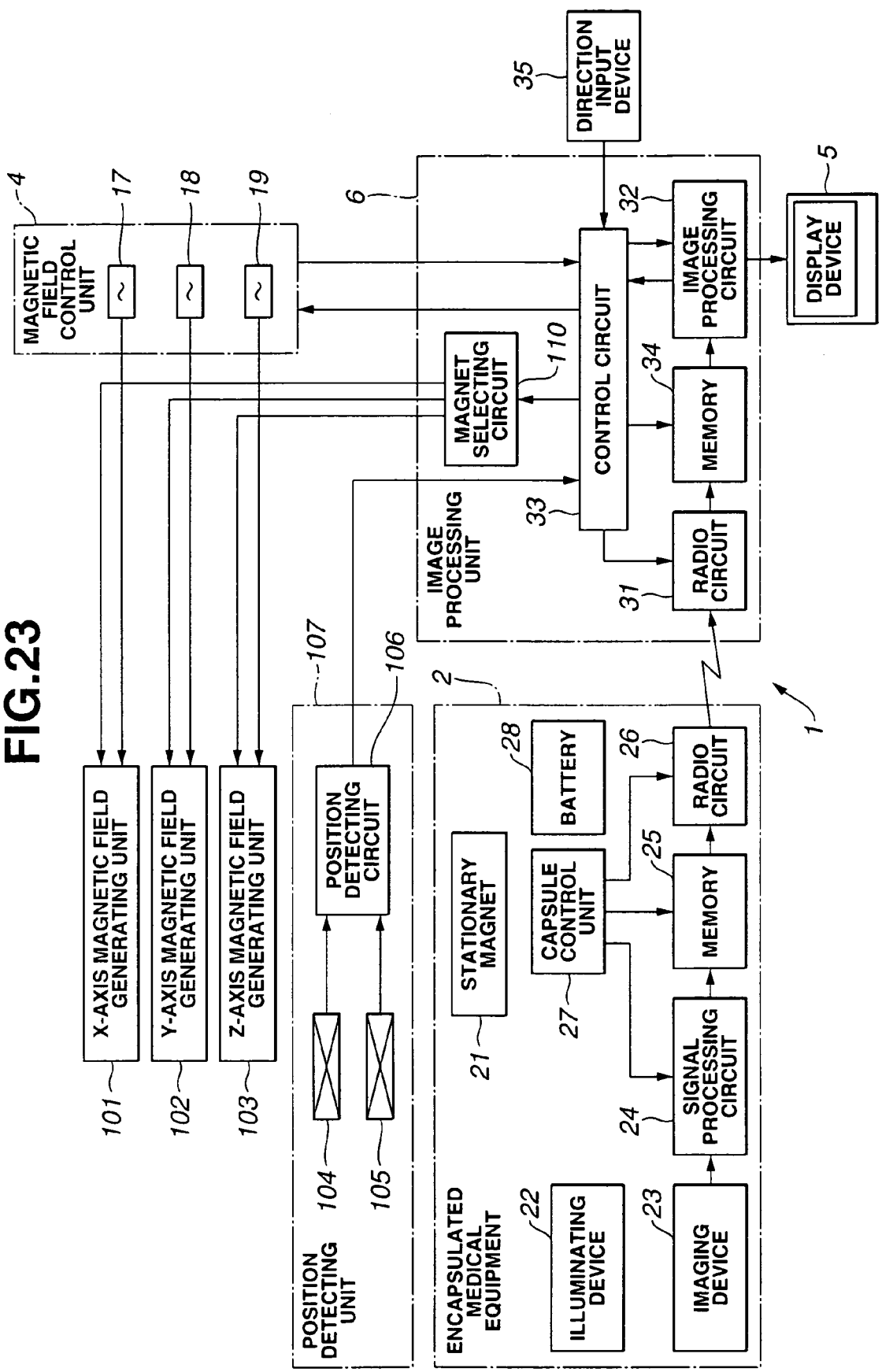
FIG. 23 to FIG. 26 are concerned with a fourth embodiment of the present invention.

As shown in FIG. 23, according to the present embodiment, a rotating magnetic field generating unit comprises: an X-axis magnetic field generating unit 101 composed of a plurality of pairs of coils; a Y-axis magnetic field generating unit 102 composed of a plurality of pairs of coils; and a Z-axis magnetic field generating unit 103 composed of a plurality of pairs of coils. Moreover, an encapsulated endoscope system in accordance with the present embodiment includes a position detecting unit 107 comprises: two triaxial sense coils 104 and 105 that detect the strength and orientation of a magnetic field induced around the stationary magnet 21; and a position detecting circuit 106 that calculates the three-dimensional position and orientation of the encapsulated endoscope 2 using detection signals sent from the triaxial isotropic sense coils 104 and 105 respectively. The position detecting circuit 106 transmits the three-dimensional position data and orientation data concerning the encapsulated endoscope 2 to the control circuit 33 in the image processing unit 6.

Moreover, the image processing unit 6 includes a magnet selecting circuit 110 that transmits a selection control signal to the X-axis magnetic field generating unit 101, Y-axis magnetic field generating unit 102, and Z-axis magnetic field generating unit 103 under the control of the control circuit 33.

Figure 24:
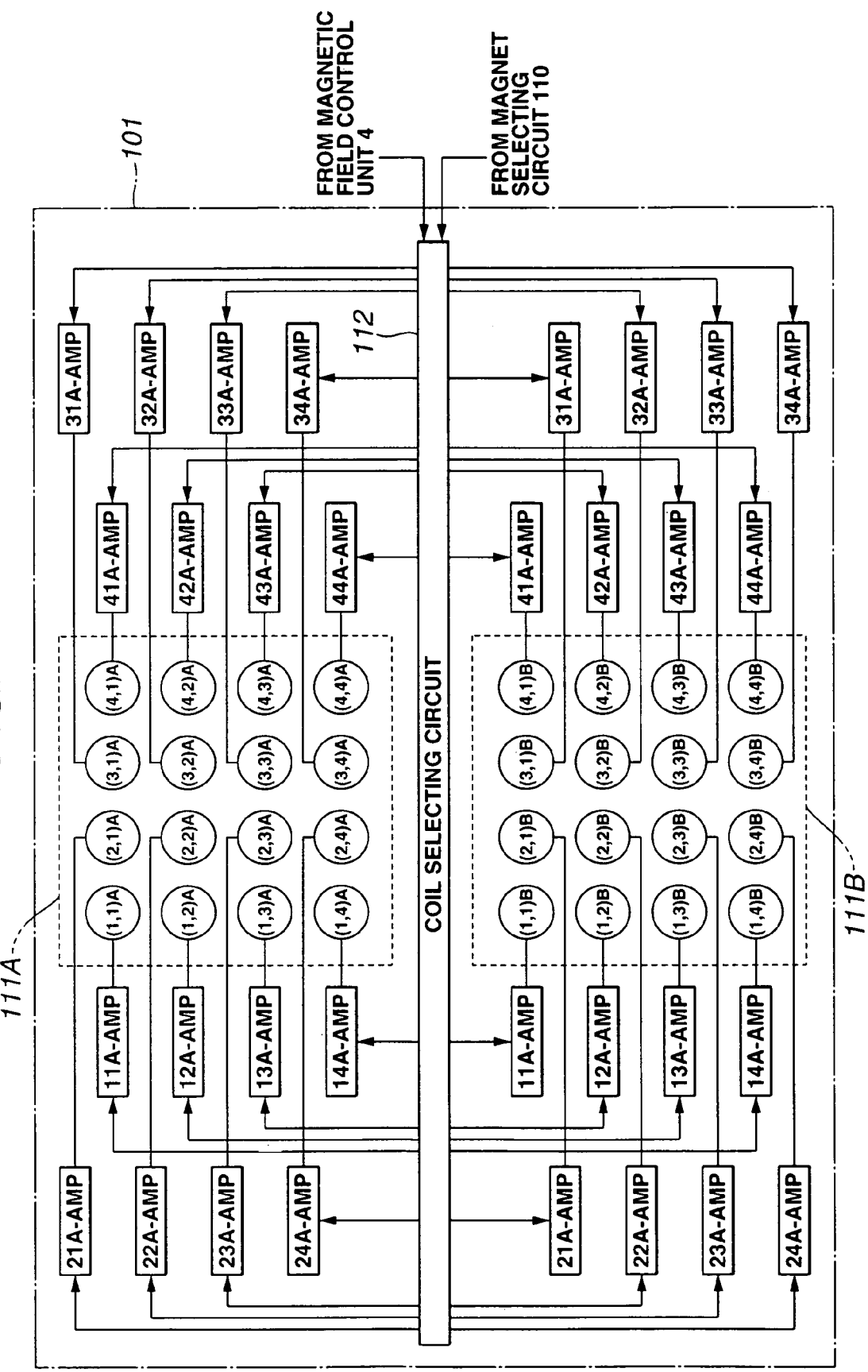

The X-axis magnetic field generating unit 101 includes, as shown in FIG. 24, a first group of coils 111A composed of a plurality of coils arranged in the form of a matrix, for example, sixteen coils (1,1)A to (4,4)A, and a second group of coils 111B composed of a plurality of coils arranged in the form of a matrix, for example, sixteen coils (1,1)B to (4,4)B. The first group of coils 111A is opposed to the second group of coils 111B, whereby opposed electromagnets (Helmholts coils for generating a rotating magnetic field) are formed.

Moreover, ijA amplifiers (where i denotes an integer ranging from 1 to 4, and j denotes an integer ranging from 1to 4) are included for selectively driving the coils (i,j)A belonging to the first group of coils 111A, and ijB amplifiers (where i denotes an integer ranging from 1 to 4, and j denotes an integer ranging from 1 to 4) are included for selectively driving the coils (i,j)B belonging to the second group of coils 111B. Herein, the coils (i,j)B belonging to the second group of coils B are driven while being paired with the coils (i,j)A respectively.

Either of the ijA amplifiers and ijB amplifiers (where i denotes an integer ranging from 1 to 4, and j denotes an integer ranging from 1 to 4) is selected and controlled by a coil selecting circuit 112. More specifically, the coil selecting circuit 112 selects the ijA amplifiers or the ijB amplifiers (where i denotes an integer ranging from 1 to 4, and j denotes an integer ranging from 1 to 4) according to a selection control signal sent from the magnet selecting circuit 110 included in the image processing unit 6 and magnetic field control signals sent from the driving amplifiers 14 to 16 included in the magnetic field control unit 4.

The Y-axis magnetic field generating unit 102 and Z-axis magnetic field generating unit 103 have the same components as the X-axis magnetic field generating unit 101 does. The description of the components will therefore be omitted. The other components are identical to those of the first embodiment.

(Operation)

In the position detecting unit 107, the two triaxial sense coils 104 and 105 detect the strength and orientation of a magnetic field induced around the stationary magnet 21 incorporated in the encapsulated endoscope 2. The position detecting circuit 106 calculates the three-dimensional position and orientation of the encapsulated endoscope 2, and transmits the three-dimensional position data and orientation data to the control circuit 33 included in the image processing unit 6.

The control circuit 33 transmits a selection signal, with which either the coils (i,j)A or coils (i,j)B (where i denotes an integer ranging from 1 to 4, and j denotes an integer ranging from 1 to 4) are selected and driven based on the three-dimensional position data, to the magnet selecting circuit 110. The magnet selecting circuit 110 in turn transmits a selection control signal to the coil selecting circuit 112, whereby either the coils (i,j)A or coils (i,j)B (where i denotes an integer ranging from 1 to 4, and j denotes an integer ranging from 1 to 4) are selected.

Figure 25:
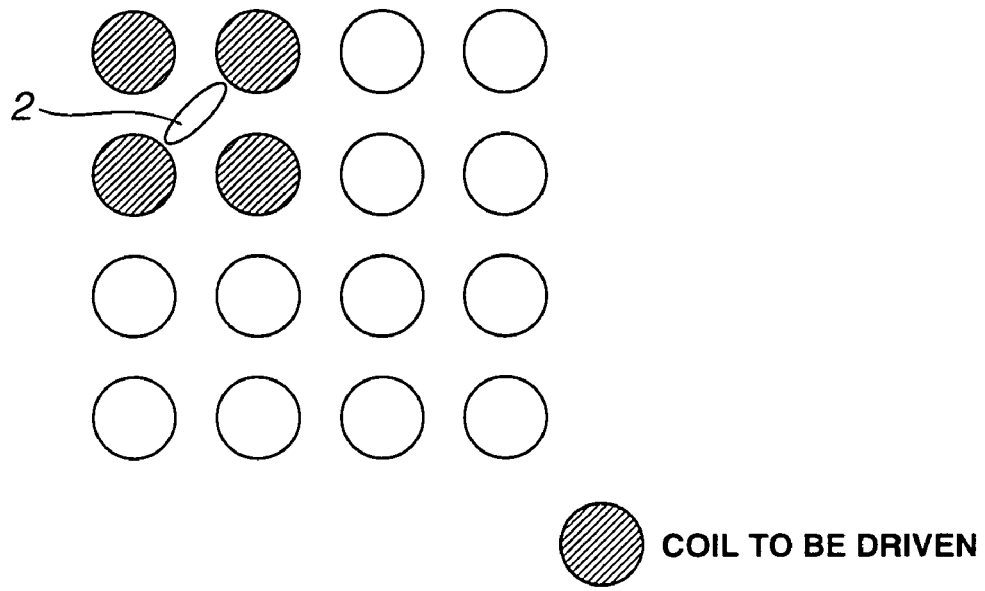

The coils (i,j)A or coils (i,j)B (where i denotes an integer ranging from 1 to 4, and j denotes an integer ranging from 1 to 4) to be driven are, for example, as shown in FIG. 25, selected based on the position of the encapsulated endoscope 2 so that a rotating magnetic field which effectively causes the encapsulated endoscope 2 to make a motion will be applied to the encapsulated endoscope 2.

A user handles the direction instructing device 35 while viewing a still image which is produced by ceasing the rotation of an image and displayed on the display device 5. The control circuit 33 included in the image processing unit 6 transmits an advancement control signal to the magnetic field control unit 4. The magnetic field control unit 4 transmits a magnetic field control signal, with which the direction of rotation of a rotating magnetic field (direction of a normal) induced by the driven coils (i,j)A or coils (i,j)B (where i denotes an integer ranging from 1 to 4, and j denotes an integer ranging from 1 to 4) is changed, to the coil selecting circuit 112.

Consequently, the encapsulated endoscope 2 makes a motion and moves. The position detecting unit 107 detects the three-dimensional position of the encapsulated endoscope 2 again. Based on the three-dimensional position data, the control circuit 33 in the image processing unit 6 controls the coil selecting circuit 112 via the magnet selecting circuit 110. Consequently, the coils (i,j)A or coils (i,j)B (where i denotes an integer ranging from 1 to 4, and j denotes an integer ranging from 1 to 4) to be driven are successively reselected so that a rotating magnetic field which effectively causes the encapsulated endoscope 2 to make a motion will be applied to the encapsulated endoscope 2.

Figure 26:
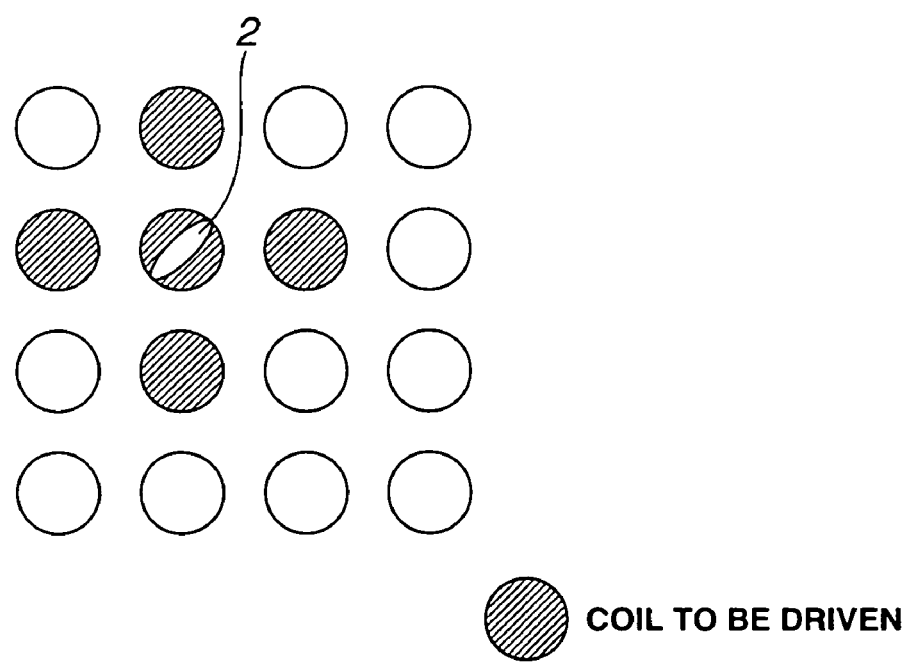

To be more specific, for example, when the encapsulated endoscope 2 is located as shown in FIG. 25, if the direction instruction device 35 is handled, a rotating magnetic field induced by the selected coils rotates. This causes the encapsulated endoscope 2 to move to a position shown in FIG. 26. Coils to be driven are reselected so that a rotating magnetic field which acts effectively on the encapsulated endoscope 2 located at the three-dimensional position will be applied to the encapsulated endoscope 2.

The operation of the present embodiment is identical to the one of the first embodiment.

(Advantages)

As mentioned above, the present embodiment provides the same advantages as the first embodiment does. In addition, a rotating magnetic field can be applied to part of a human body but not to an entire human body. A uniform rotating magnetic field can therefore be applied to the encapsulated endoscope 2. Moreover, the encapsulated endoscope 2 can be driven with low power consumption. Besides, since each coil may be small-sized, the magnetic field generating unit can be designed to be lightweight and low-cost.

A rotational driving means for rotating the encapsulated endoscope 2 or any other encapsulated medical equipment (hereinafter, simply, a capsule) has been described as a magnetic field induced by an external magnetic field generating means. The present invention is not limited to this mode. Alternatively, any other rotational driving means may be adopted. For example, a dielectric (something that exhibits polarization, such as, a capacitor) may be incorporated in the capsule as a means for rotating the capsule. An electric field may then be externally applied to the capsule so that the electric field will rotate. Thus, the capsule may be rotated.

According to the present invention, it is apparent that a wide range of different embodiments can be formed based on the invention without a departure from the spirit and scope of the invention. The present invention is limited to the appended claims but not restricted to any specific embodiment.

What is claimed is:

1. An encapsulated endoscope system comprising:
    an encapsulated endoscope configured to be inserted in a body cavity, the encapsulated endoscope comprising an imaging unit configured to image the body cavity;
    a control unit configured to generate an instruction signal for rotating the encapsulated endoscope by a predetermined amount in a desired direction;
    a driving unit configured to rotate the encapsulated endoscope by the predetermined amount in the desired direction based on the instruction signal generated by the control unit;
    an extracorporeal unit configured to receive image data sent from the imaging unit and the instruction signal generated by the control unit, and to record the instruction signal and the image data in association with each other;
    an image processing unit configured to correct an orientation of the image data based on the instruction signal and to cause a display device to display the corrected image data; and
    an information recording medium that can be freely connected to or disconnected from the extracorporeal unit and the image processing unit, wherein the image data is transferred from the extracorporeal unit to the image processing unit via the information recording medium.

2. An encapsulated endoscope system according to claim 1, wherein the image processing unit is a personal computer.

3. An encapsulated endoscope system according to claim 1, wherein the extracorporeal unit consists of a radio circuit and a control circuit.

4. An encapsulated endoscope system according to claim 1, wherein the information recording medium is a magnetic disk.

5. An encapsulated endoscope system according to claim 1, wherein the information recording medium is an optical disk.

6. An encapsulated endoscope system according to claim 1, wherein the information recording medium is an optical magnetic disk.

7. An image acquiring method for an encapsulated endoscope, the method comprising:
- capturing an image inside the body by the encapsulated endoscope;
- generating an instruction signal for rotating the encapsulated endoscope by a predetermined amount in a desired direction;
- rotating the encapsulated endoscope by the pedetermined amount in the desired direction based on the enerated instruction signal;
- producing an image data corresponding to the captured image inside the encapsulated endoscope;
- sending the image data to an extracorporeal unit;
- receiving the image data and the instruction signal by the extracorporeal unit and recording the instruction signal and the image data in association with each other;
- correcting an orientation of the image data based on the instruction signal and causing a display device to display the corrected image data by an image processing unit; and
- transferring the image data from the extracorporeal unit to the image processing unit via an information recording medium that can be freely connected to or disconnected from the extracorporeal unit and the image processing unit.

8. An image acquiring method for an encapsulated endoscope according to claim 7, wherein the step of receiving the image data by the extracorporeal unit comprises receiving the image data by radio.

9. An image acquiring method for an encapsulated endoscope, the method comprising:
- capturing an image inside the body;
- generating an instruction signal for rotating the encapsulated endoscope by a predetermined amount in a desired direction;
- rotating the encapsulated endoscope by the predetermined amount in the desired direction based on the generated instruction signal;
- producing an image data based on the captured image;
- sending the image data by radio;
- receiving the image data extracorporeally;
- storing the instruction signal and the received image data in association with each other in a disconnectable memory;
- transferring the image data by the disconnectable memory to a display device; and
- correcting orientation of the image data based on the instruction signal and displaying the image corresponding to the corrected image data.

* * * * *